United States Patent
Lichtenberg et al.

(10) Patent No.: US 10,704,016 B2
(45) Date of Patent: Jul. 7, 2020

(54) DEVICE FOR PROPAGATING MICROTISSUES

(71) Applicant: INSPHERO AG, Schlieren (CH)

(72) Inventors: Jan Lichtenberg, Unterengstringen (CH); Wolfgang Moritz, Bassersdorf (CH); Jens Kelm, Zürich (CH)

(73) Assignee: INSPHERO AG, Schlieren (CH)

( * ) Notice: Subject to any disclaimer, the term of this patent is extended or adjusted under 35 U.S.C. 154(b) by 109 days.

(21) Appl. No.: 15/740,894

(22) PCT Filed: Jul. 1, 2016

(86) PCT No.: PCT/EP2016/065571
§ 371 (c)(1),
(2) Date: Dec. 29, 2017

(87) PCT Pub. No.: WO2017/001680
PCT Pub. Date: Jan. 5, 2017

(65) Prior Publication Data
US 2018/0187136 A1 Jul. 5, 2018

(30) Foreign Application Priority Data
Jul. 1, 2015 (GB) .................. 1511544.7

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/12* (2013.01); *C12M 23/20* (2013.01); *C12M 25/01* (2013.01);
(Continued)

(58) Field of Classification Search
CPC .... B01L 2300/0829; B01L 2300/0832; C12M 23/12; C12M 25/04
See application file for complete search history.

(56) References Cited

U.S. PATENT DOCUMENTS 5,180,555 A      1/1993  Monget
5,260,032 A *   11/1993  Muller .................. B01L 3/5021
                                                                356/244
(Continued)

FOREIGN PATENT DOCUMENTS

EP        1621890 A1   2/2006
GB        2507744 A    5/2014
(Continued)

OTHER PUBLICATIONS

Messner et al. "Multi-cell type human liver microtissues for hepatotoxicity testing." Archives of Toxicology 87.1 (2013): 209-2013. (Year: 2013).*
(Continued)

*Primary Examiner* — Nathan A Bowers
(74) *Attorney, Agent, or Firm* — Ballard Spahr LLP

(57) ABSTRACT

Disclosed are devices for propagating at least one microtissue, methods for manufacturing such devices, and the use us such devices, said devices comprise at least one well, wherein said at least one well comprises an open upper section comprising an open upper end and an open lower end, and a lower section comprising an open upper end and a bottom end, wherein the upper section and the lower section are in fluid communication, and wherein the bottom end of the lower section of at least one well of said plurality of wells is provided with a well bottom, said lower section of said at least one well has a smaller cross-sectional area than the open upper section of the same well.

17 Claims, 6 Drawing Sheets

(51) Int. Cl.
  *C12M 1/32* (2006.01)
  *C12M 1/12* (2006.01)
  *C12M 1/26* (2006.01)
  *C12N 5/00* (2006.01)

(52) U.S. Cl.
  CPC ............ *C12M 25/14* (2013.01); *C12M 33/10* (2013.01); *C12N 5/0062* (2013.01)

(56) References Cited

U.S. PATENT DOCUMENTS

| | | |
|---|---|---|
| 5,801,055 A | 9/1998 | Henderson |
| 2003/0032071 A1 | 2/2003 | Wang |
| 2005/0136546 A1 | 6/2005 | Berndt |
| 2011/0220567 A1* | 9/2011 | Kreuwel ............... B01L 3/5085 210/222 |
| 2013/0029422 A1 | 1/2013 | Goral et al. |
| 2014/0106395 A1 | 4/2014 | Fattinger |
| 2018/0284102 A1* | 10/2018 | Jaime ................. B01L 3/50255 |

FOREIGN PATENT DOCUMENTS

| | | |
|---|---|---|
| WO | 2006040871 A1 | 4/2006 |
| WO | 2009003487 A1 | 1/2009 |
| WO | 2013056019 A1 | 4/2013 |
| WO | 2015001397 A1 | 1/2015 |
| WO | WO-2015001397 A1 * | 1/2015 ............ C12M 21/06 |

OTHER PUBLICATIONS

International Search Report and Written Opinion dated Nov. 18, 2016 by the International Searching Authority for Patent Application No. PCT/EP2016/065571, which was filed on Jul. 1, 2016 and published as WO 2017/001680 on Jan. 5, 2017 (Inventor—Lichtenberg et al.; Applicant—Insphero AG) (10 pages).

Search Report dated Apr. 21, 2016 by the Intellectual Property Office of the United Kingdom for Patent Application No. GB1511544.7, which was filed on Jul. 1, 2015 and published as GB2539935 on Jan. 4, 2017 (Inventor—Lichtenberg et al.; Applicant—Insphero AG) (4 pages).

* cited by examiner

DEVICE FOR PROPAGATING MICROTISSUES

CROSS-REFERENCE TO RELATED APPLICATIONS

This is a U.S. National Phase Application of International Application No. PCT/EP2016/065571, filed Jul. 1, 2016, which claims the benefit of Provisional GB Application No. 1511544.7, filed on Jul. 1, 2015, which is hereby incorporated herein by reference in its entirety.

The present invention relates to the field of in-vitro cultivation of cells, more specifically to the generation and/or propagation of microtissues, and in particular to devices for generating and or propagating microtissues, to methods of manufacturing such devices, and to the use of said devices.

Microtissues comprise a plurality of homotypic or heterotypic cells, preferably mammalian cells, more preferably human cells. In microtissues, cells grow and/or interact within their surroundings in all three dimensions in an artificially-created environment. Such 3D cell cultures more closely resemble the in vivo surroundings of the cells. Microtissues are also designated as spheroids, and provide a more accurate model system for cellular, physiological and/or pharmaceutical studies than cells grown in conventional two dimensional cultures.

For conventional two dimensional cell cultures, the cells are propagated in cell culture flasks, petri dishes or wells of a multiwell plate. These cell culture devices permit or even promote adherence of the cells to the inner lining of the culture vessel, i.e. the flask, dish or well. Multiwell plates became widely used in two dimensional cell cultures due to the small sample volumes required for cell propagation, and for their suitability for simultaneously propagating a plurality of different cell samples within a single device.

For microtissue formation, it is necessary to prevent adhesion of the cells to the inner lining of the culture vessel, because their adherence to the culture vessel's inner lining would impair the desired three dimensional aggregation of the cells within the culture medium.

Various approaches have been made for generating microtissues and preventing adherence of the cells to the inner lining of a culture vessel. One approach for forming microtissues is the scaffold-free hanging-drop method, wherein the cells are propagated in a hanging drop. Multiwell plates for simultaneous formation of a plurality of microtissues pursuant to the scaffold-free hanging-drop method are commercially available under the tradename GravityPLUS™ from InSphero AG, Schlieren, CH.

Another approach for generating microtissues is utilizing multiwell plates comprising non-adhesively coated wells, for example the GravityTRAP™ plate of InSphero AG, Schlieren, CH. This is a special non-adhesively coated 96-well multiwell plate which is designed to receive and accommodate microtissues for long-term cultivation and analysis. The microtissues are positioned in an observation chamber at the bottom of each well, wherein the vertical axis of said observation chamber is centered with the vertical axis of the remainder of the well.

However, utilizing non-adhesively coated multiwell plates for propagating microtissues require extraordinary caution when handling the multiwell plates, in particular upon removal or exchange of the culture medium. The non-adherence of the microtissue renders them vulnerable to be aspirated inadvertently along with the culture medium in case of undue care. The likelihood of microtissues for being aspirated also poses problems for automatic handling procedures in propagating microtissue cell cultures.

An object of the present invention was therefore to provide a device for propagating microtissues, wherein the risk of aspirating the microtissue is avoided or at least significantly reduced, wherein the microtissue remains largely undisturbed when the culture medium is replace with fresh medium, and which device may therefore also be used in automatic microtissue cultivation procedures.

According to a first aspect, the invention provides a device for propagating at least one microtissue, said device comprising at least one well.

According to a second aspect, the invention provides a method for manufacturing a device for propagating at least one microtissue.

According to a third aspect, the invention provides the use of a device according to the first aspect for propagating microtissues.

According to a further aspect, the invention provides a method for generating and/or propagating microtissues utilizing the device of the first aspect.

According to a further aspect, the invention provides a system for generating and/or propagating microtissues, said system comprising a device according to the first aspect of the invention.

According to a further aspect, the invention provides the use of the system for generating and/or propagating microtissues.

According to yet another aspect, the invention provides a method of generating and/or propagating microtissues utilizing the system.

Figure 1:
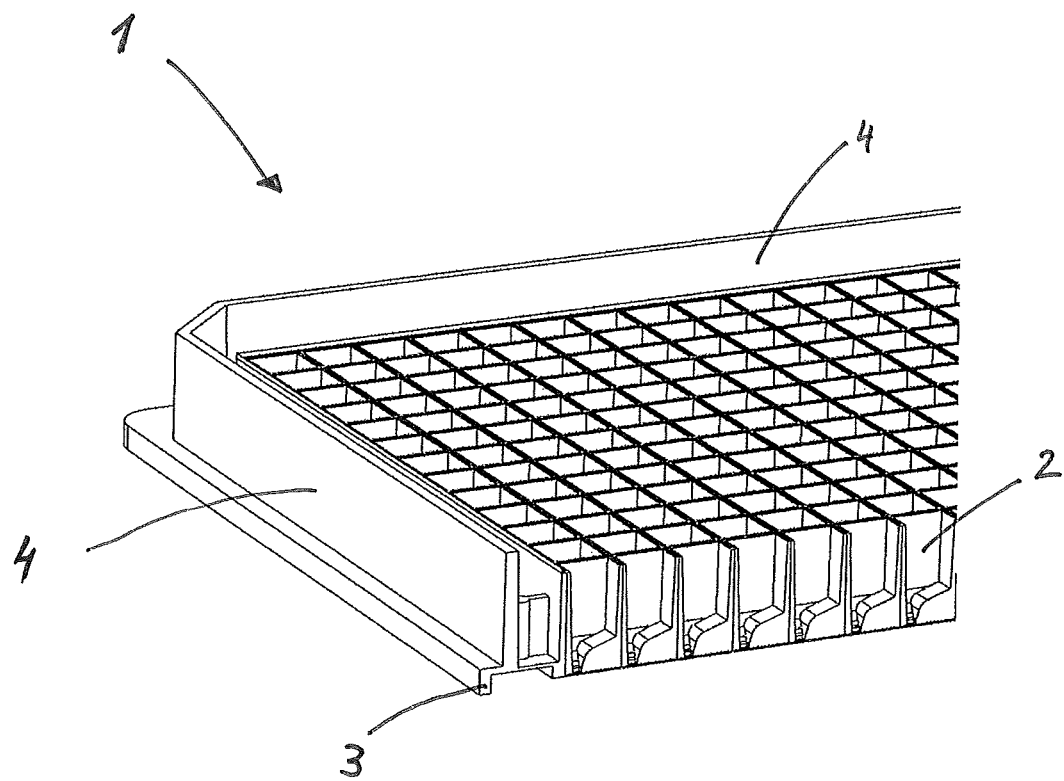
FIG. 1 shows a cross-sectional perspective view of an embodiment of the device according to the invention, wherein the device is configured as a multiwell plate comprising an array of wells.

According to the first aspect, the present invention provides a device for propagating at least one microtissue, said device comprising at least one well. Said at least one well comprises an open upper section which comprises an open upper end and an open lower end, and a lower section comprising an open upper end and a bottom end, wherein the upper section and the lower section are in fluid communication with each other, and wherein the bottom end of the lower section of said at least one well is provided with a well bottom, said lower section of said at least one well having a smaller cross-sectional area than the open upper section of the well, preferably a smaller cross-sectional area than the open upper end and/or the open lower end of the open upper section.

The open upper section of the at least one well is configured for receiving and removing any bulk culture medium that is filled into or removed from the well. The open upper section thus constitutes the reservoir for the bulk of the culture medium within the well for the cells in culture within the well. The open upper section is therefore considered to be the liquid handling compartment of the well. The open upper end of the open upper section is configured as fluid receiving aperture of the well.

The open upper section comprises an open lower end. In an embodiment, the walls of the open upper section are essentially perpendicular with respect to the plane of an even surface the device is placed on. Preferably the inner lining extending from the upper end of the open upper end to the open lower end of the open upper section is essentially vertical when the device is placed on an even horizontal surface. In another embodiment, the walls of the open upper section taper and thereby configure a conical open upper section. Tapering of the open upper section may be towards the open upper end or towards the open lower end of the open upper section of the at least one well.

In an embodiment, the open upper section of the at least one well may have a circular, oval, triangular, quadratic, rectangular or polygonal cross section at its open upper end and/or its open lower end and/or anywhere between the open upper end and the open lower end of the open upper section.

The lower section of the at least one well has an open upper end which is in fluid communication with the open lower end of the open upper section such that fluid provided in the open upper section may flow into the lower section. The lower section comprises a bottom end comprising a well bottom.

The lower section of the at least one well may have a circular, oval, triangular, quadratic, rectangular or polygonal cross section at its open upper end and/or its bottom end and/or anywhere between the open upper end and the open lower end of the open upper section.

Typically, the walls of the lower section are essentially perpendicular with respect to the plane of an even surface the device is placed on. Preferably the inner lining of the lower section is essentially vertical when the device is placed on an even horizontal surface.

The lower section of said at least one well has a smaller cross-sectional area than the open upper section of the well, preferably a smaller cross-sectional area than the open upper end and/or the open lower end of the open upper section. The term "cross-sectional area" refers to the area of a virtual plane being disposed perpendicular to the longitudinal/vertical axis of the section.

The lower section of the well constitutes the microtissue formation chamber of said well. Providing a well with a lower section having smaller diameter has the advantage that less culture medium is required for propagating the microtissue in the well, compared to propagating a microtissue in a conventional well. In addition, microscopic inspection of the microtissue is facilitated, because extensive search for the microtissue in the well is avoided. The presence of a microtissue formation chamber at the lower end of a well enables automatic microscopic inspection and/or morphological analysis of the microtissues.

In another and/or alternative embodiment, the lower section of the at least one well is excentrically arranged with respect to the longitudinal axis of the open upper section of the same well. The longitudinal axis of the open upper section extends perpendicular to the bottom plane of the well from the center of the open upper end of the upper section to the center of the open lower end of the upper section. Thus, the longitudinal axis corresponds to the vertical axis of the open upper section. From the top view perspective, the vertical axis of the lower section, which extends from the center of the open upper end of the lower section to the center of the bottom end of the lower section, is not centered with the vertical axis of the open upper section.

The lumen of the at least one well of the device is defined by its inner lining of well's bottom and wall(s). The wall(s) of the at least one well may be transparent, translucent or colored, preferably black or white. In an additional and/or alternative embodiment, the wall(s) of the at least one well is/are impervious to light, e.g. impervious to visible light and/or impervious to ultra violet light.

Wells possessing walls being impervious to visible and/or UV light are advantageous for microscopic inspection of the microtissues or microtissues, because scattering of light from and/or to—for example—adjacent wells is prevented. Thereby, microscopic analysis of the microtissue in a well is simplified and facilitated.

The at least one well comprises a bottom: Said bottom defines the lower end of the lower section of the well. In an embodiment, said bottom is flat and preferably transparent and/or thin walled. In an additional and/or alternative embodiment, the bottom of the well permits microscopic inspection of the well's lower section's content, i. e. the microtissue, by means of an inverted microscope. The bottom of the well may either be made of the same material as the wall(s) of the well, or the bottom of the well may consist of a different material than that constituting the well's wall(s). In an additional and/or alternative embodiment, the bottom of the at least one well is provided by a layer having an essentially homogeneous thickness of between about 100 μm to about 250 μm, preferably a homogeneous thickness of about 180 μm.

In another embodiment, the bottom of the at least one well comprises a pit. Said pit may have a V-shape, a U-shape or may be present in the form of an inverted pyramid. Providing the bottom of the at least one well with a pit allows keeping the concentration of cells high when a very small volumes of cell suspension is employed for generating a microtissue.

In another and/or alternative embodiment, the at least one well further comprises an intermediate section. Said intermediate section is disposed between the open upper section and the lower section, more specifically between the open lower end of the open upper section and the open upper end of the lower section. The intermediate section provides a flow path between the upper section and the lower section.

In an additional and/or alternative embodiment, the intermediate section is configured to provide a pipetting stage. The pipetting stage is configured as a platform within the well, said platform has a slope such that any fluid applied to the platform can drain off into the lower section. The slope of the pipetting platform has an angle of at least 5°.

The slope of the pipetting stage has an angle of not more than 45°, preferably of not more than 35°, more preferably of not more than 25°, and most preferably of not more than 15°.

Most preferably, the slope of the pipetting platform has an angle of 10°.

The angle of the slope is to be understood as the angle between the plane or the pipetting stage and the plane of the horizontal cross sectional area, which is parallel to the plane of the multiwell plate where the pipetting stage is in contact with the wall of the upper section of the well.

In another and/or alternative embodiment, the intermediate section further comprises a chute. Said chute is provided between the pipetting stage and the lower portion of a well.

The chute may be configured as an area and/or as a groove.

The chute has a slope, wherein the slope of the chute is steeper than the slope of the pipetting stage within the same well.

The pipetting stage and/or the chute may be present in a well on only one inner side of the well, on two adjacent inner sides of the well, on three inner sides of the well, or on all four or all inner sides of the well.

In an additional and/or alternative embodiment, at least a portion of the at least one well comprises an ultra-low adhesion surface. In an additional and/or alternative embodiment, at least the lower section of the at least one well is provided with an ultra-low adhesion surface. The ultra-low adhesion surface may consist of a coating layer consisting of a hydrogel such as agarose, or of a coating layer consisting of 2-methacryloyloxyethyl phosphorylcholine (MPC). Providing at least the lower section with an ultra-low adhesion surface prevents adhesion of the cells to the inner lining of the microtissue formation chamber. This aids in promoting microtissue formation within the microtissue formation chamber.

In an additional and/or alternative embodiment at least a portion of the bottom of the lower section of at least one well comprises a hydrophobic surface. Providing the bottom of the at least one well with a small hydrophobic area allows the placement and formation of a miniscule hydrogel/cell droplet which does not deliquesce. Thus, a droplet keeps its configuration which sustains while any hydrogel present in the droplet polymerizes.

In an embodiment, the device for propagating a microtissue comprises a plurality of wells, wherein at least one well, preferably all wells are configured as described herein before for the at least one well.

In an additional and/or alternative embodiment, the plurality of wells are configured as a row of wells. Said row of well preferably comprises two, four, six, eight, ten or twelve wells, preferably in consecutive order.

In an additional and/or alternative embodiment of the device comprising a plurality of wells, at least one well, preferably all wells of the device comprise a ring structure at the upper end of the open upper section. Said ring structure extends in perpendicular direction from the upper end of the wells.

Preferably, said ring structure has the same cross-section as the open upper section at its open upper end. The presence of such ring structures prevents drops from spreading into neighboring wells, in particular when microtissues are generated in a scaffold-free hanging drop environment utilizing the device of the present invention by having it turned upside down while the microtissue forms.

In an additional embodiment, the ring structures of adjacent wells are configured such that they are not in contact with each other.

In an alternative and/or additional embodiment, the device for propagating a microtissue is configured as a multiwell plate, preferably as a multiwell plate of the standard SBS/ANSI format.

In another and/or alternative embodiment, said multiwell plate comprises 96 wells, preferably in an 8×12 array. In an alternative embodiment, the multiwell plate comprises 384 wells, preferably in a 16×24 array. In a further embodiment, said multiwell plate comprises 1536 wells, preferably in a 32×48 array.

In an embodiment of a 96-well version of the multiwell plate, the length of the inner edge or inner diameter of the open end of the open upper section is preferably at least 5.0 mm, more preferably at least 6.0 mm, and most preferably at least 7.0 mm. The length of the inner edge or inner diameter of the open end of the open upper section is less than 8.5 mm, preferably less than 8.0 mm, more preferably less than 7.5 mm.

In an embodiment of a 96 well version of the multiwell plate, the length of the inner edge or inner diameter of the lower section is at least 0.1 mm, preferably at least 0.25 mm, and more preferably at least 0.5 mm. The length of the inner edge or inner diameter of the lower section is less than 4.5 mm, preferably less than 4.0 mm, more preferably less than 2.0 mm, and most preferably less than 1.5 mm.

In an embodiment of the 96-well version of the multiwell plate, the lower section has a height of at least 0.1 mm, preferably of at least 0.375 mm, more preferably of at least 0.5 mm. The height of the lower section preferably does not exceed 1.5 mm.

In an additional and/or alternative embodiment of the 96-well version of the multiwell plate, the lower section has a volume of at least 0.0007 µl, preferably a volume of about 0.4 µl, and more preferably a volume that does not exceed 30.4 µl.

In an additional and/or alternative embodiment of the 96-well version of the multiwell plate, the ratio of the cross sectional areas of the lower section and the open upper end of the upper section is at least 1:1.57 and preferably less than 1:9200. More preferably, the ratio of the cross sectional areas of the lower section and the open upper end of the upper section is in the range of from about 1:50 to about 1:83.

In an embodiment of a 384-well version of the multiwell plate, the length of the inner edge or inner diameter of the open end of the open upper section is preferably at least 3.0 mm, more preferably at least 3.5 mm, and most preferably at least 3.7 mm. The length of the inner edge or inner diameter of the open end of the open upper section is less than 4.0 mm.

In an embodiment of a 384-well version of the multiwell plate, the length of the inner edge or inner diameter of the lower section is at least 0.1 mm, preferably at least 0.25 mm, and more preferably at least 0.5 mm. The length of the inner edge or inner diameter of the lower section is less than 2.5 mm, preferably less than 2.0 mm, and most preferably less than 1.5 mm.

In an embodiment of the 384-well version of the multiwell plate, the lower section has a height of at least 0.1 mm, preferably of at least 0.375 mm, more preferably of at least 0.5 mm. The height of the lower section preferably does not exceed 1.5 mm.

In an additional and/or alternative embodiment of the 384-well version of the multiwell plate, the lower section has a volume of at least 0.0007 µl, preferably a volume of about 0.17 µl, and more preferably a volume that does not exceed 9.4 µl.

In an additional and/or alternative embodiment of the 384-well version of the multiwell plate, the ratio of the cross sectional areas of the lower section and of the open upper end of the upper section is at least 1:1.83 and preferably less than 1:2040. More preferably, the ratio of the cross sectional areas of the lower section and the open upper end of the upper section is in the range of from about 1:19 to about 1:31.

In a preferred embodiment of the 96-well version of the multiwell plate, the inner edge of inner diameter has a length of 8.0 mm, the inner edge or inner diameter of the lower section has a length of 1.0 mm, and the lower section has a height of 0.5 mm.

In a preferred embodiment of the 384-well version of the multiwell plate, the inner edge of inner diameter has a length of 3.7 mm, the inner edge or inner diameter of the lower section has a length of 0.75 mm, and the lower section has a height of 0.375 mm.

In an alternative and/or additional embodiment, the multiwell plate comprises a rim. Said rim is positioned on the outer edge of at least one side of the multiwell plate, preferably on opposite sides, either the long or the short sides, or on all four sides of the multiwell plate thereby constituting a circumferential rim. During use of the multiwell-plate, water may be supplied to the rim. As said rim is covered by a lid covering the multiwell plate, the moisture of the gaseous phase within the wells may be kept sufficiently high for preventing undesired evaporation of culture medium from the wells.

In an additional and/or alternative embodiment, the multiwell plate comprises a continuous and/or integrated bottom configured as a layer having an essentially homogeneous thickness of between about 100 µm to about 250 µm, preferably a homogeneous thickness of about 180 µm.

In additional embodiment, said layer comprises a plurality of pits, said plurality of pits are arranges in array such that each well of the multiwell plate is provided with a bottom comprising a pit. Said pit may have a V-shape, a U-shape or may be present in the form of an inverted pyramid.

According to the second aspect, the invention provides a method for manufacturing a device for propagating microtissues as described. The method comprises separate manufacturing of the wall(s) of the at least one well, and of the bottom of the at least one well. In the method, the wall(s) of the at least one well are manufactured by suitable methods. In an embodiment of manufacturing the wall(s), they are manufactured by means of injection molding or by means of 3D-printing utilizing suitable polymeric material. The resulting product comprises a through bore having a wide aperture at one end and a narrow aperture at the opposite end. Said wide end corresponds to the open upper end of the open upper section of the at least one well, whereas the narrow aperture corresponds to the lower end of the lower section.

The bottom of the at least one well is manufactures separately. In an embodiment, the bottom is manufactured in form of a film or disk. Said film or disk has an essentially homogeneous thickness, preferably in the range of about 100 µm to about 250 µm, more preferably of about 180 µm.

In an embodiment for providing a bottom to the at least one well or the wells of a multiwell plate, wherein the bottom of the at least one well or the wells comprise a pit, the film representing the bottom is subjected to deep drawing, blow molding or thermo forming. Said deep drawing, blow molding or thermo forming deforms the film and provides V-shaped, U-shaped pits or pits in form of an inverted pyramid. For embodiments of the device comprising a plurality and/or array of well, the film is provided with a plurality and/or array of pits such that said pits align with the lower ends of the lower sections of the wells of the device upon providing the wells with a bottom.

Subsequently to the separate manufacturing of the wall(s) and the bottom, the bottom of the device is attached to the prefabricated wall(s) by gluing or sealing the film or disk to the plane bearing the narrow apertures.

In an alternative embodiment, the device is manufactured by insertion molding in that the film or disk is provided as an insert, and that the wall(s) is/are produced then generated on one face of the insert by injection molding utilizing a suitable polymeric material, thereby closing the lower aperture(s) resulting in a device for propagating microtissues as described herein before.

According to the third aspect, the invention comprises the use of a device as described herein before for forming and/or propagating microtissues. Thus, the invention also concerns methods for generating and/or propagating microtissues by using a device according to the first aspect of the invention.

The term "propagating" as used in the instant disclosure refers to all aspects of cultivating cells and/or generating microtissues. The term "propagating" as used herein comprises the cultivation of cells including their multiplication, development, proliferation and maturation. Thus, "propagating" also comprises the formation and/or growth of microtissues. The term "propagating" as used herein also comprises the maintenance, storage and/or shipping of cells and/or microtissues in culture.

In an embodiment, the method for generating a microtissue comprises the steps of:
  supplying a suspension of cells in a culture medium to at least one well of a device according to the first aspect;
  accumulating the cells in the lower section of the at least one well, preferably by centrifugation;
  maintaining the device in an essentially horizontal or in a slanted position until a microtissue has formed.

In an additional and or alternative embodiment, the suspension of cells is a suspension of cells in a hydrogel to immediately provide a three dimensional environment. Polymerization of the hydrogel provides a three dimensional structure to be colonized by the cells.

In another embodiment, the method for generating a microtissue comprises the steps of
  supplying a suspension of cells in a minimal volume of a hydrogel to at least one well of a device according to the first aspect;
  whereas the hydrogel/cell suspension is positioned directly onto the bottom of the lower section of the at least one well;
  adding medium after the hydrogel has polymerized; and
  propagating the device at least until a microtissue has formed in the at least one well.

In another embodiment, the method for generating a microtissue comprises the steps of
  supplying a hydrogel into the lower section of at least one well of a device according to the first aspect;
  supplying a suspension of cells in a culture medium to the at least one well of the device;
  accumulating the cells in the lower section of the at least one well, preferably by centrifugation; and
  propagating the device until the cells have migrated into the hydrogel and formed a microtissue in the at least one well.

In another embodiment, the method for generating a microtissue comprises the steps of:
  supplying a suspension of cells in a culture medium to at least one well of a device according to the first aspect;
  turning the device upside down,
  propagating the device in inverted position until a microtissue has formed in the at least one well;

turning the device into its upright position; and
transferring the microtissue into the lower section of the well, preferably by centrifugation.

In the use of the device and/or the method for forming and/or propagating microtissues, a suspension of cells in an appropriate culture medium is provided into at least one well of the device according to the first aspect, and supplied into the at least one well of the device.

Embodiments of the method wherein a hydrogel and subsequently the cells, or a suspension of cells in a hydrogel are supplied to the lower section of a well of the device, only minute amounts thereof are required. This permits the use of very small (minimal) volumes, e.g. between 0.1 µl and 2 µl per well, and a high cell density, e.g. between about 50 to about 1,000 cells in said small volume.

In an embodiment, the device is turned upside down and kept in this inverted position for a prescribed period of time under appropriate environmental conditions such that the cells proliferate and aggregate. The cells will then aggregate to a microtissue in the lower end of the hanging drop of culture medium, said drop hanging down from the open upper end of the open upper section of the at least one well. The ring structure around the open upper end of the upper section will prevent drops spreading into neighboring wells.

When the microtissue has formed in the hanging drop of the at least one well, the multiwell plate can be inverted to its upright position again, and can subsequently be centrifuged at low speed such that the microtissue in the at least one well is exposed to low g forces which forces the microtissue into the microtissue formation chamber without affecting the microtissue. Any excess culture medium may be removed from the at least one well in that the tip of a pipette is inserted into the at least one well slightly above the pipetting stage, and that the medium is then aspirated off using the pipette.

Supplying fluid to a well and/or aspirating fluid from the well by means of a pipette whose tip is positioned above the pipetting stage within the well prevents the microtissue from being in the direct flow path of the fluid. Thereby, the microtissue is exposed to weaker forces, and is less affected by necessary cultivation steps. In addition, placing the tip of the pipette onto the pipetting stage within the well provides a gap on one side of the pipette tip—due to the slope of the pipetting stage—through which the fluid is aspirated. Due to the angle of the slope, the gap is too small for a microtissue to pass.

According to further aspects, the invention provides a system for forming and propagating microtissues, the use of said system for forming and propagating microtissues, and a method for forming and propagating microtissues by using said system.

The system comprises a device according to the first aspect of the invention as described herein before, said device being configured as a multiwell plate, the first multiwell plate of the system, comprising an array of wells. The system further comprises a second multiwell plate. Said second multiwell plate comprises a frame formed by the side walls, and an array of a plurality of wells. The array of a plurality of wells in the second multiwell plate corresponds to the array of wells of the multiwell according to the first aspect. The second multiwell plate, also designated as the corresponding multiwell plate, can be placed or mounted on top of the first multiwell plate such that each of the wells of the further multiwell plate is aligned with a well of the multiwell plate according to the first aspect.

The wells of the second multiwell plate do not comprise a well bottom, but a bottleneck between an open upper portion and an open lower portion of each well. This bottleneck is configured to permit a fluid such as a culture medium from running there through into the lower portion of the well. However, in absence of fluid supply from the upper portion, a drop of fluid remains in the lower portion of the well and hanging down from the lower edge of the lower portion. Such multiwell plates are commercially available under the trade name GravityPLUS™, from InSphero AG, Schlieren, CH.

The second multiwell plate may be used for simultaneous formation of microtissues, either already assembled to the multiwell plate of the first aspect, or to another type of plate support, in a hanging drop method. If present on other support, the further multiwell plate may be transferred to the first multiwell plate of the system, and the microtissues that have formed may be transferred from their hanging drops into the wells of the first multiwell plate, either by centrifugation of the assembly or by supply of an additional amount of medium to each well of the further multiwell plate bearing a microtissue.

The present invention will be further described with respect to particular embodiments and with reference to the drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be further described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Referring to FIG. 1, an embodiment of a device according to the invention, configured as a multiwell plate (1), is shown in a cross sectional perspective view. The multiwell plate (1) comprises a plurality of wells (2). The wells (2) are arranged in an array. The array of wells (2) is surrounded by a circumferential side wall (4) extending essentially upright from the lower edge (3). The cross-section extends along the median line of a row of wells and illustrates the inner configuration of the wells.

Figure 2:
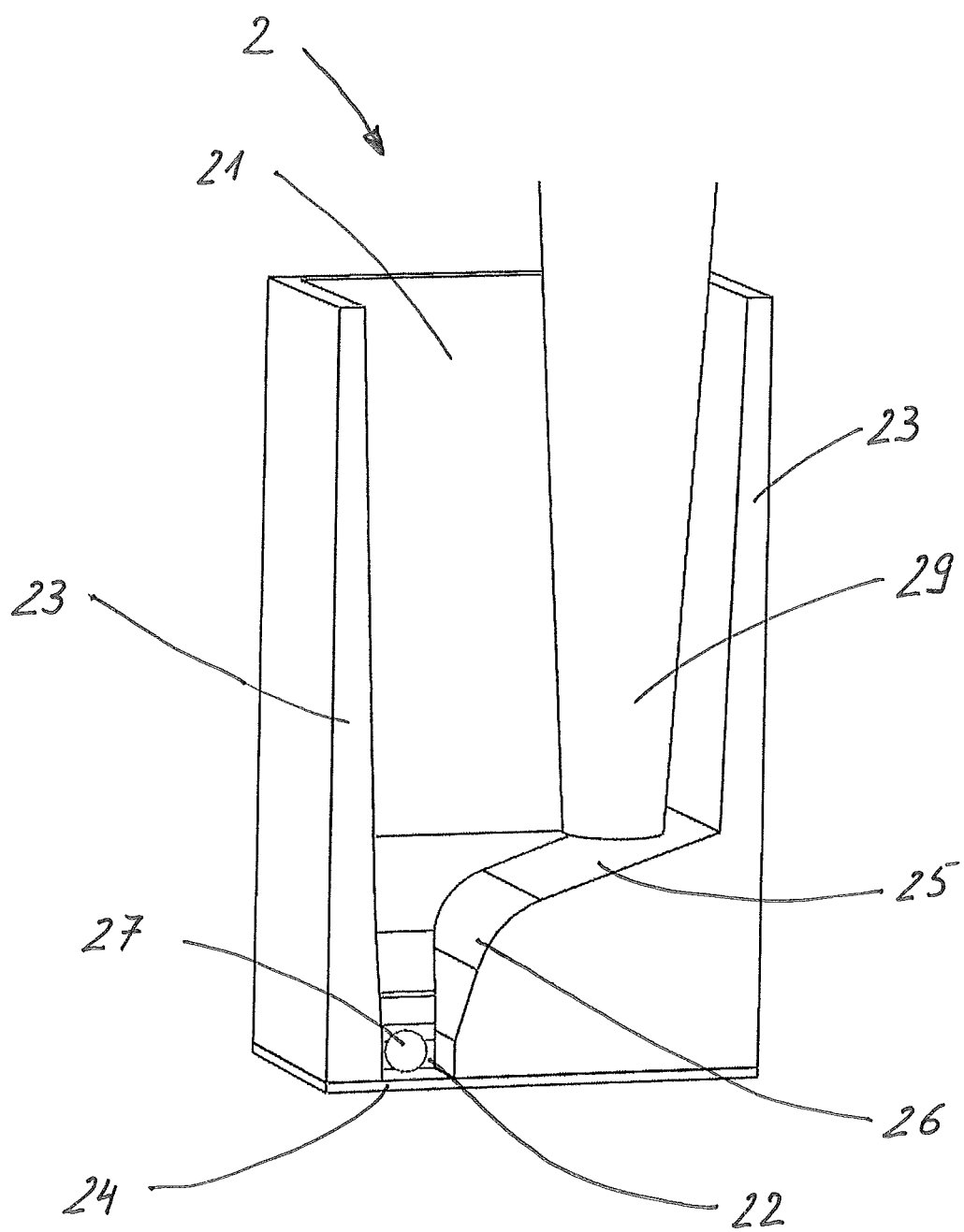
FIG. 2 represents a cross-sectional perspective view of an embodiment of the device according to the invention.

FIG. 2 displays a cross-sectional drawing of a well (2) of an embodiment of the multiwell plate. The well (2) comprises an open upper section (21) and a lower section (22). The lower section (22) constitutes the microtissue formation chamber and holds a microtissue (27). The well (2) is defined by its side walls (23) and the well bottom (24). The well (2) is configured to have a pipetting stage (25) and a chute (26) at one side of the rectangular well. The pipetting stage (25) provides a slope such that any fluid applied thereto can run off. The chute (26) provides a transition between the lower edge of the pipetting stage and the lower section of the well. The chute (26) has a larger inclination than the slope of the pipetting stage (25).

For adding or aspirating medium from the well, a pipette tip (29) is inserted into the well (2) at the side of the pipetting stage (25) such that any fluid to be supplied to the well hits the pipetting stage first, before flowing smoothly downwards the pipetting stage and along the chute (26) into the lower section (22) of the well. Thereby, the microtissue is not directly present within the flow path of any fluid supplied to or being aspirated from the well. The pipetting stage (25) provides a slope upon which the vertical positioning of the pipette tip (29) onto this slope forms a gap between the orifice of the pipette tip (29) and the pipetting stage (25). At optimal inclination of the slope, the gap is small enough to prevent a microtissue to be aspirated inadvertently, while assuring efficient aspiration of fluid.

Figure 3A:
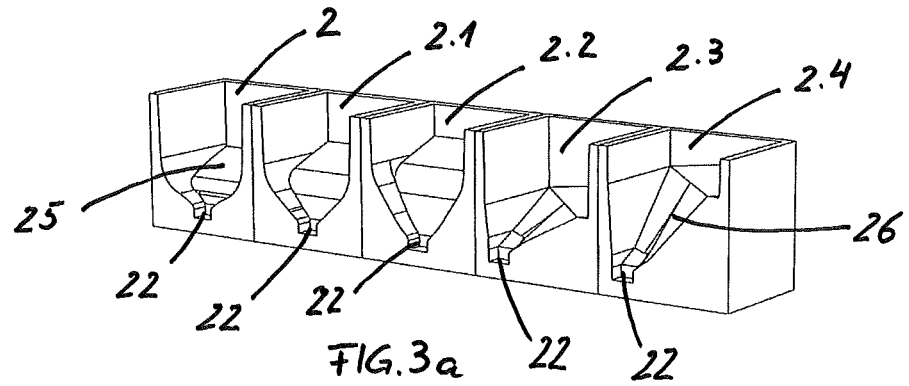
FIG. 3a represents a cross-sectional perspective view of different well configurations that may be present in an embodiment of a device according to the invention.
Figure 3B:
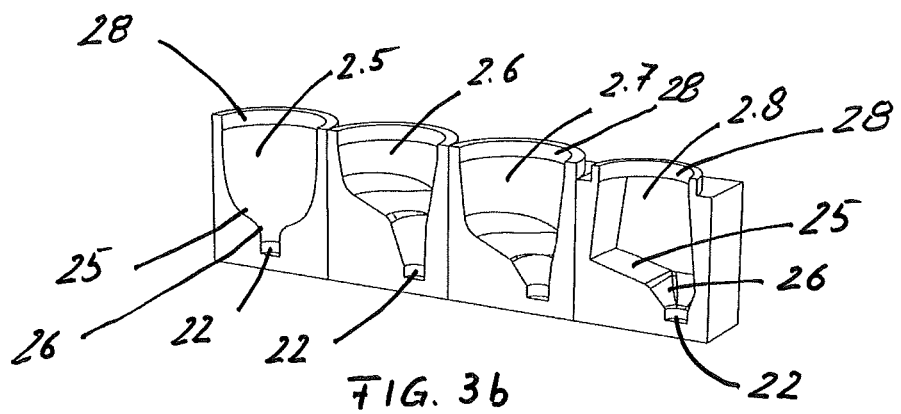
FIG. 3b represents a cross-sectional perspective view of different well configurations that may be present in an embodiment of a device according to the invention.
Figure 3C:
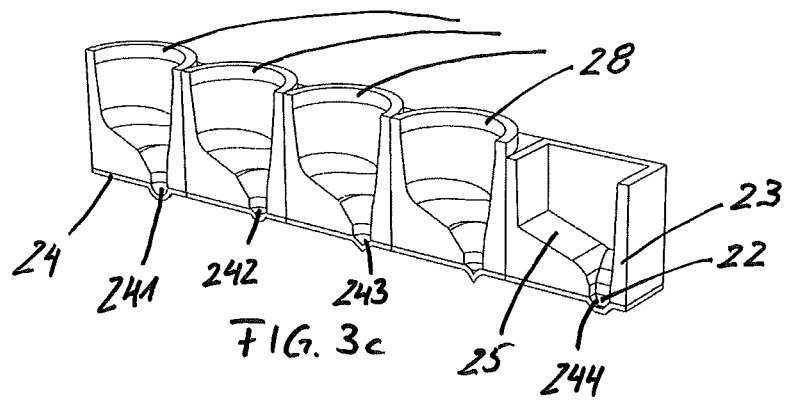
FIG. 3c represents a cross-sectional perspective view of different well configurations that may be present in an embodiment of a device according to the invention.

FIGS. 3*a*, 3*b* and 3*c* represent a cross-sectional perspective views of different well configurations that may be present an embodiment of a multiwell plate according to the invention. FIG. 3*a* displays a row of five wells (2, 2.1, 2.2, 2.3, 2.4) having a square cross-sectional area at the open upper end of the open upper section of the well. FIG. 3*b* displays a row of four wells (2.5, 2.6, 2.7, 2.8) having a circular cross-sectional area at the open upper end of the open upper section.

FIG. 3*c* display a row of wells which are provided with a bottom (24) in form of a separately manufactured film. Said bottom is provided with pits (241, 242, 243, 244), wherein the position of the pits (241, 242, 243, 244) corresponds to the position of the lower sections (22) of the wells such that the lower section of each of the wells is provided with a pit. The presence of a pit in the bottom of the well prevents spreading of the fluid therein and aides in forming and/or maintaining the three-dimensional structure of a spheroid.

FIGS. 3*b* and 3*c* further display embodiments of wells possessing a ring structure (28) at the open upper end of the open upper section. The outer edges of the ring structures (28) of adjacent wells may be in contact with each other, such as—for example—the ring structures of wells 2.5 and 2.6 in FIG. 3*b*, or the ring structures of adjacent wells may not be in contact with each other such as exemplified by the ring structures (28) of wells 2.7 and 2.8 in FIG. 3*b*. Such ring structures stabilize hanging drops and prevent spreading of fluid from one drop to a neighboring drop when the device is used in inverted position for hanging drop cultures.

Figure 4:
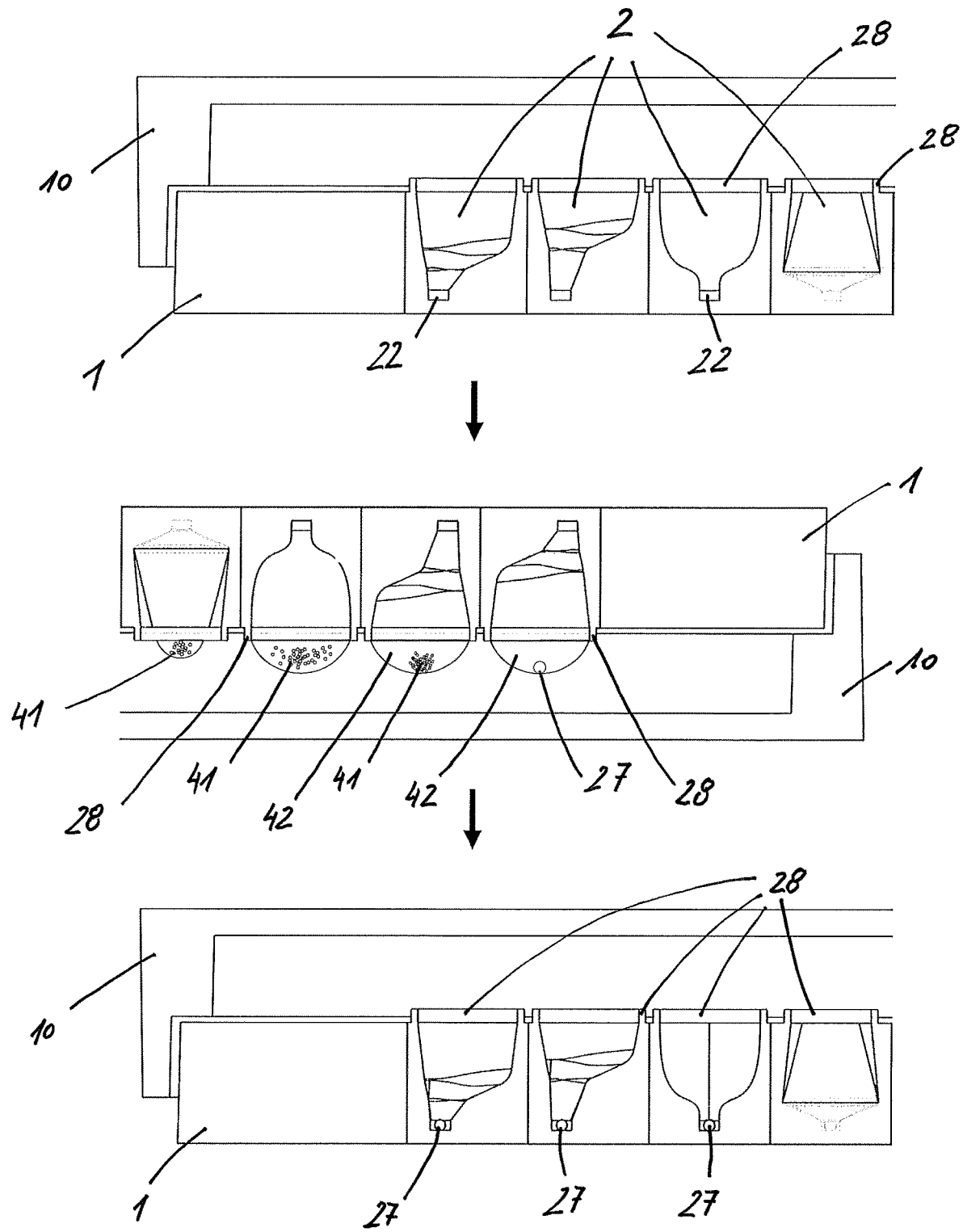
FIG. 4 shows a cross sectional view of different well configurations that may be present in an embodiment of a device according to the invention, and illustrates how microtissues can be generated and propagated using the device.

FIG. 4 illustrates an embodiment of a method of forming microtissues by using a multiwell plate according to the first aspect. In the upper part of the figure, a portion of a multiwell plate (1) is shown in a cross-sectional view. The portion as shown includes four wells (2) possessing different well configurations. For forming a microtissue (27), a suspension of cells (41) in a suitable culture medium (42) in provided into a well, and the multiwell plate, optionally including a lid (10) or seal, is turned upside down as illustrated in the middle part of the figure. The cells (41) in the culture medium (42) can aggregate and form a microtissue (27) at the lower, hanging portion of the culture medium (42). This represents a scaffold-free, hanging-drop method for forming microtissues.

Once the microtissue (27) has formed, the multiwell plate (1) is returned to the original upside up position, and optionally by centrifugation at low speed, the microtissue (27) within a well (2) is lead into the microtissue formation chamber (22). Excess medium may then be aspirated off, and the microtissue may be further propagated.

Figure 5:
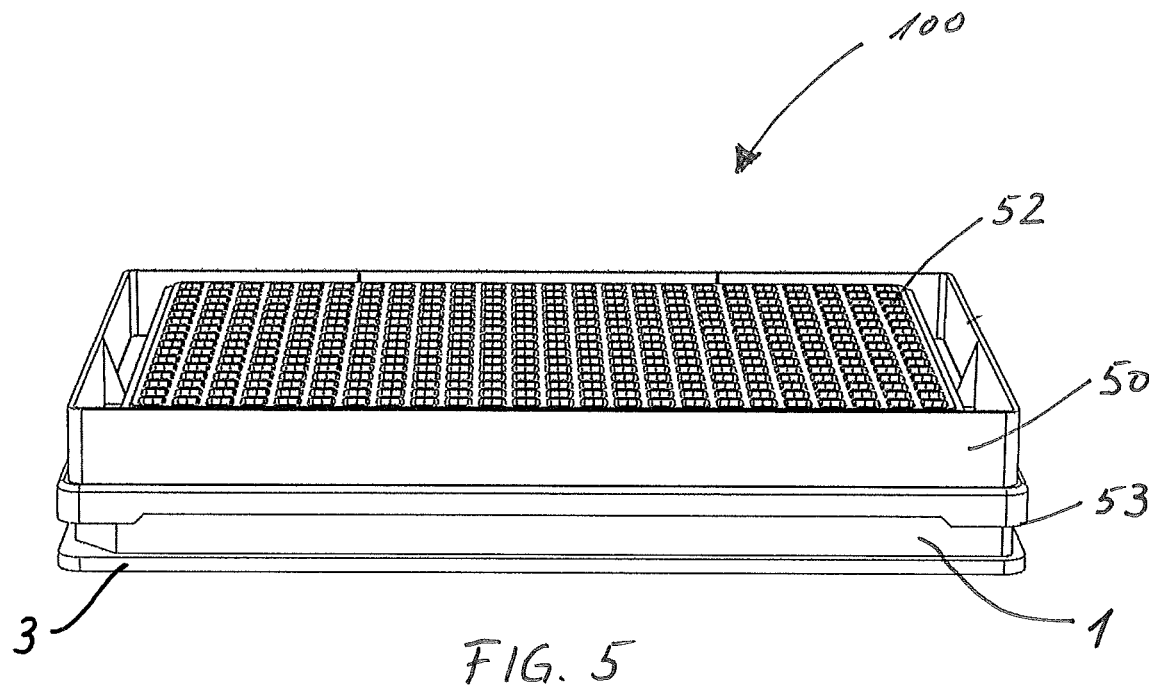
FIG. 5 is a perspective drawing of an embodiment of a system according to the invention, wherein the device is present in form of a multiwell plate, and wherein the system further comprises a scaffold-free hanging-drop plate.

FIG. 5 is a perspective drawing of a system (100) comprising a multiwell plate (1), and a corresponding second multiwell plate (50) which comprises an array of a plurality of wells (52). The corresponding multiwell plate (50) can be placed on top of the multiwell-plate (1), preferably in form-fitting manner. As the array of wells (52) is essentially identical to the array of wells within the multiwell plate (1), each of the wells (52) is aligned with a well (2) of the multiwell plate (1).

Figure 6:
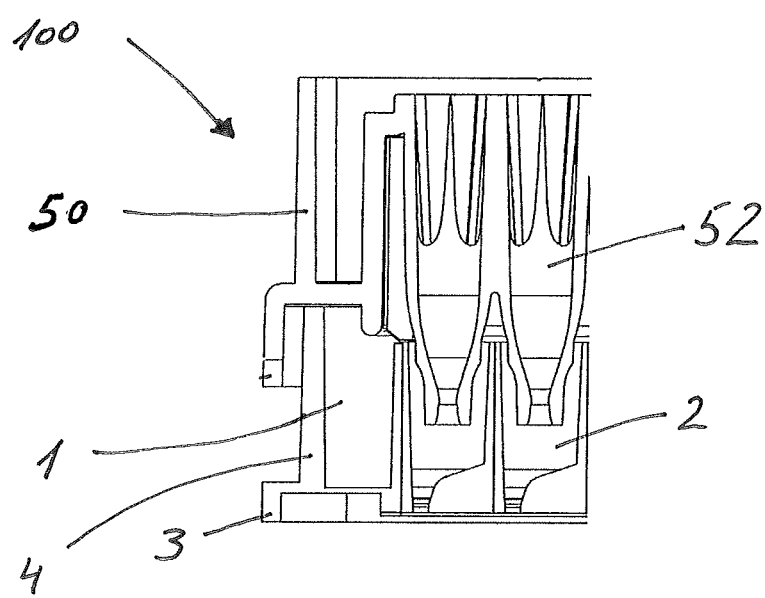
FIG. 6 is a cross-sectional drawing of a portion of the system as shown in FIG. 5.

FIG. 6 is an enlarged cross sectional view of a portion of the assembly as shown in FIG. 5. As can be inferred, each well (52) of the corresponding multiwell plate (50) is aligned with a well (2) of the multiwell plate (1). Correct assemble of the system is facilitated by the configuration of the corresponding multiwell plate's lower edge (53) which permits correct assembly and prevents inadvertent slipping of the corresponding multiwell plate.

Multiwell plate (1) comprises a circumferential frame 4 encompassing the array of wells (2). Said frame 4 provides a rim between the frame (4) and the outer wells of the array of wells. Said rim may hold a fluid such as water or for aiding in maintaining humidity of the gaseous phase in the wells of the multiwell plate.

The multiwell plate (1) further comprises a circumferential edge (3) the multiwell plate (1) resides on when placed onto a support in upright position. The edge (3) is preferably configured such that the lower ridge of the edge (3) is lower than the bottom (24) of the wells (2). This configuration prevents the bottom (24) of the wells (2) from contacting a plane support said multiwell plate (1) is typically placed on, and thereby prevents scratching of the bottom which in turn is advantageous upon microscopic inspection of the microtissues within the wells (2).

Figure 7:
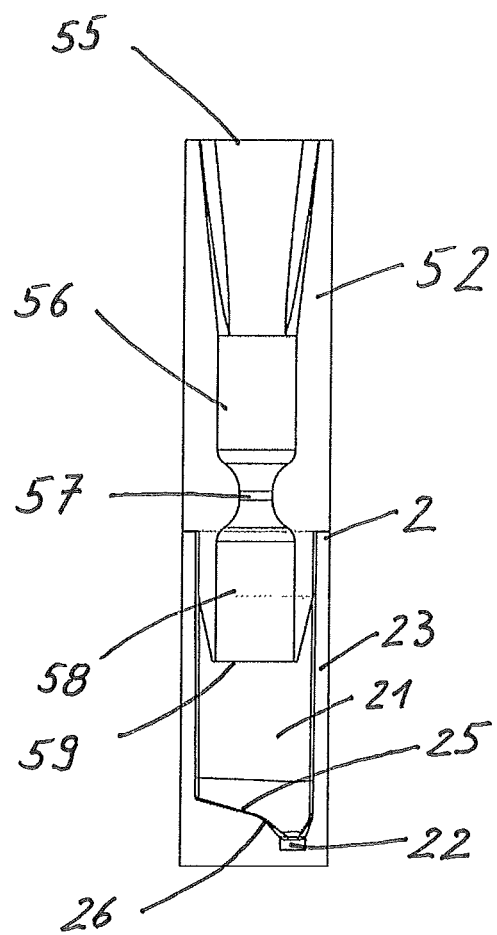
FIG. 7 is a cross-sectional drawing of a portion of another system including a device according to the invention in form of a well, and a portion of a scaffold-free hanging-drop plate.

FIG. 7 is an enlarged cross-sectional drawing of a well alignment provided by an assembly shown in FIGS. 5 and 6. Each wells of the corresponding multiwell plate comprises an inlet opening (55), an open upper portion (56), an open lower portion (57), and a bottleneck disposed between the open upper and open lower portion. An appropriate amount of culture medium containing cells, can be supplied to the well (52), runs through the bottle neck (57) and is kept hanging down from the lower edge (59) of the lower portion (58). A microtissue may then be formed in the hanging drop.

The corresponding multiwell plate (100) may thus be used to simultaneously form a plurality of microtissues in a scaffold-free method within a drop of medium hanging down from each of the wells (52). Upon assembly to the multiwell plate (1), the microtissues may be transferred to the wells (2) of multiwell plate (1) either by gently centrifuging the assembly of multiwell plate (1) and corresponding multiwell plate (50) or in that an additional amount of medium is supplied to each well (52) through the inlet opening (55). Thereby, the drop of culture medium hanging down from the lower edge (59) of each well (52) and containing a microtissue is forced to fall down into the corresponding well (2) of multiwell plate (1).

The invention claimed is:

1. A multiwell plate comprising a plurality of wells for propagating at least one microtissue, wherein each of said plurality of wells comprises an upper section with an upper opening of the well, a lower section with a closed well bottom, and a single narrowing from the upper opening to the closed well bottom, the narrowing being comprised in an intermediate section arranged between the upper section and the lower section, wherein the upper section and the lower section are in fluid communication, and wherein the lower section of each well has a smaller cross-sectional area than the upper section of the same well, wherein the lower section is eccentrically arranged with respect to the longitudinal axis of the upper section of each well, wherein the intermediate section further comprises a pipetting stage and a chute, the pipetting stage and the chute being comprised in the single narrowing of the well, wherein said pipetting stage has an inclination and said chute being provided between the pipetting stage and the lower section, and wherein the chute has a gradually increasing inclination, the inclination being larger than the slope of the pipetting stage.

2. The multiwell plate according to claim 1, wherein the inclination of the pipetting stage has an angle of at least 5°, and of not more than 45°.

3. The multiwell plate according to claim 1, wherein the device comprises a row of wells or an array of wells.

4. The multiwell plate according to claim 1, wherein said multiwell plate comprises an array of 96 wells, an array of 384 wells or an array of 1536 wells.

5. The multiwell plate according to claim 4, wherein the multiwell plate is a standard SBS/ANSI format multiwell plate.

6. The multiwell plate according to claim 1, wherein at least the lower section of at least one well of the plurality of wells is provided with an ultra-low attachment coating.

7. The multiwell plate according to claim 1, wherein the wall(s) of at least one well of the plurality of wells are made of a different material than the bottom of the multiwell plate.

8. The multiwell plate according to claim 1, wherein the well bottom of each of said plurality of wells is arranged at the same distance from a bottom of the multiwell plate.

9. The multiwell plate according to claim 1, wherein the multiwell plate has a continuous plane bottom.

10. The multiwell plate according to claim 1, wherein the lower section of each of said plurality of wells has a height not exceeding 1.5 mm.

11. A system for generating and/or propagating microtissues, said system comprising a first scaffold-free hanging drop multiwell plate and a corresponding second multiwell plate as defined by claim 1.

12. A method of manufacturing a multiwell plate as defined in claim 1, wherein the wall(s) of the at least one well and the bottom of the multiwell plate are manufactured separately, said bottom being manufactured in form of a film or disk, and wherein the at least one well is subsequently provided with said bottom.

13. A method for generating a microtissues, the method comprising the steps of:
   a) supplying a suspension of cells in a minimal volume of a hydrogel to at least one well of the multiwell plate of claim 1;
      whereas the hydrogel/cell suspension is positioned directly onto the bottom of the lower section of the at least one well;
   b) adding medium after the hydrogel has polymerized;
   c) propagating the device at least until a microtissue has formed in the at least one well.

14. The method for generating a microtissue according to claim 13, wherein the suspension of cells is a suspension of cells in a hydrogel.

15. A method for generating a microtissue, the method comprising the steps of:
   a) supplying a suspension of cells in a culture medium to at least one well of a multiwell plate according to claim 1;
   b) accumulating the cells in the lower section of the at least one well, preferably by centrifugation;

c) maintaining the multiwell plate in an essentially horizontal or in a slanted position until a microtissue has formed.

16. A method for generating a microtissue, the method comprising the steps of:
   a) supplying a hydrogel into the lower section of at least one well of a multiwell plate according to claim 1;
   b) supplying a suspension of cells in a culture medium to the at least one well of the multiwell plate;
   c) accumulating the cells in the lower section of the at least one well, preferably by centrifugation;
   d) propagating the multiwell plate until the cells have migrated into the hydrogel and formed a microtissue in the at least one well.

17. A method for generating a microtissues, the method comprising the steps of:
   a) supplying a suspension of cells in a culture medium to at least one well of the multiwell plate according to claim 1;
   b) turning the multiwell plate upside down;
   c) propagating the device in inverted position until a microtissue has formed in the at least one well;
   d) turning the multiwell plate into its upright position; and
   e) transferring the microtissue into the lower section of the well, preferably by centrifugation.

* * * * *